United States Patent
Sylvestre et al.

(10) Patent No.: US 12,082,827 B2
(45) Date of Patent: Sep. 10, 2024

(54) MINIMALLY INVASIVE SURGERY TARGETING GUIDES AND METHODS OF USE

(71) Applicant: Stryker European Operations Limited, Carrigtwohill (IE)

(72) Inventors: Pierre-Luc Sylvestre, Grenchen (CH); Alexis Christen, Herzogenbuchsee (CH); Katja Stucki, Baden (CH); Matthias Paulisch, Roggwil (CH)

(73) Assignee: Stryker European Operations Limited, Carrigtwohill (IE)

( * ) Notice: Subject to any disclaimer, the term of this patent is extended or adjusted under 35 U.S.C. 154(b) by 0 days.

(21) Appl. No.: 17/874,438

(22) Filed: Jul. 27, 2022

(65) Prior Publication Data
US 2022/0361900 A1    Nov. 17, 2022

Related U.S. Application Data

(63) Continuation of application No. 17/110,562, filed on Dec. 3, 2020, now Pat. No. 11,432,832.

(51) Int. Cl.
*A61B 17/17* (2006.01)
*A61B 17/00* (2006.01)

(52) U.S. Cl.
CPC ........... *A61B 17/1728* (2013.01); *A61B 2017/00424* (2013.01)

(58) Field of Classification Search
CPC .................................................. A61B 17/1728
See application file for complete search history.

(56) References Cited

U.S. PATENT DOCUMENTS

| | | | |
|---|---|---|---|
| 8,043,297 B2* | 10/2011 | Grady, Jr. | A61B 17/1728 606/98 |
| 8,100,952 B2* | 1/2012 | Matityahu | A61B 17/80 606/280 |
| 8,641,741 B2 | 2/2014 | Murashko, Jr. | |
| 9,011,457 B2 | 4/2015 | Grady, Jr. et al. | |
| 9,131,968 B2 | 9/2015 | Cavallazzi et al. | |
| 9,138,245 B2 | 9/2015 | Mebarak | |
| 9,155,575 B2 | 10/2015 | Wenk et al. | |
| 9,649,118 B2 | 5/2017 | Mebarak | |
| 9,730,711 B2 | 8/2017 | Wolf et al. | |
| 10,028,778 B2 | 7/2018 | Venturini et al. | |
| 10,111,692 B2 | 10/2018 | Baker et al. | |
| 10,111,712 B2 | 10/2018 | Chegini et al. | |
| 11,432,832 B2* | 9/2022 | Sylvestre | A61B 17/1728 |

(Continued)

FOREIGN PATENT DOCUMENTS

WO    2017149026 A2    9/2017

OTHER PUBLICATIONS

AxSOS Targeting System: Femur Fractures: Operative Technique—Distal Lateral Femur, copyright 2011 Stryker, Stryker Trauma AG, Selzach, Switzerland, 28 pages.

*Primary Examiner* — Tracy L Kamikawa
(74) *Attorney, Agent, or Firm* — Lerner David LLP

(57) ABSTRACT

A targeting system for use with a bone plate includes a body having an upper side and an opposite lower side, a first lateral side and a second opposite lateral side, a first plurality of holes extending through the upper and lower sides and arranged in a first pattern, a second plurality of holes extending through the first and second lateral sides and arranged in a different second pattern.

9 Claims, 14 Drawing Sheets

(56) References Cited

U.S. PATENT DOCUMENTS

| | | |
|---|---|---|
| 2011/0301655 A1 | 12/2011 | Price et al. |
| 2013/0072988 A1 | 3/2013 | Hulliger |
| 2014/0066996 A1 | 3/2014 | Price et al. |
| 2016/0374738 A1* | 12/2016 | Smith ................ A61B 17/1725 606/71 |
| 2018/0256222 A1 | 9/2018 | Lueth et al. |
| 2019/0076174 A1* | 3/2019 | Tiongson ............... A61B 17/86 |
| 2019/0133611 A1 | 5/2019 | Schreiber et al. |
| 2019/0328407 A1 | 10/2019 | Cunliffe et al. |

* cited by examiner

MINIMALLY INVASIVE SURGERY TARGETING GUIDES AND METHODS OF USE

CROSS-REFERENCE TO RELATED APPLICATIONS

This application is a continuation of U.S. application Ser. No. 17/110,562, filed on Dec. 3, 2020, now U.S. Pat. No. 11,432,832, the disclosure of which is incorporated herein by reference.

BACKGROUND OF THE INVENTION

The present disclosure relates to a bone plating system and methods of use thereof for the fixation of fractures of the bone, such as the femur, tibia, humerus and radius. More specifically, the present disclosure includes a bone plate targeting system including a targeting guide or block for screw placement within a bone plate.

When a bone is damaged or fractured, bone plates are commonly attached to the outside surface of the damaged bone to stabilize the area and promote healing of the bone. Generally, the plates have a bone contacting side and a side facing away from the bone with a plurality of holes extending through the two surfaces. The plates are often designed for polyaxial and/or monoaxial screw placement.

In order to accurately place the screws, targeting guides are typically used. In the instance of monoaxial placement, there exists a need for a targeting guide that provides accurate placement of the screws while accommodating more than one plate configuration, thereby advantageously reducing the amount of tools required for a given surgery.

SUMMARY OF THE INVENTION

The present disclosure includes a targeting system for accurately implanting bone screws within a bone plate. The targeting system includes a targeting guide block. The block has different sides extending that have different patterns corresponding to holes of a different bone plate. The holes of each side of the targeting block align axially with holes of the respective bone plate, based on the side of the targeting block that is utilized (facing the user). Opposing upper and lower sides of the block are designed to correspond to left and right versions of a bone plate of a first size and/or shape. The opposing lateral sides of the block are designed to correspond to left and right versions of a bone plate of a second size and/or shape. Accordingly, the targeting block is designed to accurately place screws within four different plates.

A first aspect of the disclosure includes a targeting guide for a bone plate. The targeting guide includes a body having an upper side and an opposite lower side, a first lateral side and a second opposite lateral side, a first plurality of holes extending through the upper and lower sides and arranged in a first pattern, a second plurality of holes extending through the first and second lateral sides and arranged in a different second pattern.

In other embodiments, the first plurality of holes and the second plurality of holes may be configured to receive bone screws therethrough. The first plurality of holes and the second plurality of holes may be configured to receive a monoaxial sleeve. The first pattern may include pairs of diagonal holes. The second pattern may include pairs of diagonal holes. The first pattern may include less holes than the second pattern. The first pattern of the targeting guide may align with a first pattern of holes of a first bone plate. The second pattern of the targeting guide may align with a second pattern of holes of a second bone plate different from the first bone plate. The second bone plate may be longer than the first bone plate. The body may be rectangular. The body may comprise at least one connection hole on each of the upper and lower sides and the first and second lateral sides of the body. The connection hole may have a different shape than each of the first holes and second holes. Each connection hole may be positioned at a proximal end of the block. One of the upper side and the lower side of the body may correspond to a left femur bone plate and the other side of the upper side and the lower side may correspond to a right femur plate.

Another aspect of the present disclosure includes a system for attaching a bone plate to bone. The targeting guide includes a body having an upper side and an opposite lower side, a first lateral side and a second opposite lateral side, a first plurality of guide holes extending through the upper and lower sides and arranged in a first pattern, a second plurality of guide holes extending through the first and second lateral sides and arranged in a different second pattern. The system further includes a first bone plate defining a first plurality of plate holes, and a second bone plate defining a second plurality of plate holes having a different pattern than the first plurality of plate holes. When the targeting guide is attached to the first bone plate, the first plurality of guide holes align with the first plurality of plate holes, and when the targeting guide is attached to the second bone plate, the second plurality of guide holes align with the second plurality of plate holes.

In other embodiments, each one of the first plurality of guide holes may include a central axis and each one of the first plurality of plate holes may include a central axis, the central axes of the first plurality of guide holes being coaxial with the central axes of the first plurality of plate holes being coaxial when the targeting guide is attached to the first bone plate. Each one of the second plurality of guide holes may include a central axis and each one of the second plurality of plate holes may include a central axis, the central axes of the second plurality of guide holes being coaxial with the central axes of the second plurality of plate holes when the targeting guide is attached to the second plate. The system may include a monoaxial sleeve having a proximal end received within any one of the holes of the targeting guide and a distal end received within an axially aligned hole of the bone plate. The first bone plate and the second bone plate each may have an oblong hole and the targeting guide has a connection hole. The system may further include a support having a distal end configured to attach to the oblong hole of the first plate and of the second plate and a proximal end configured to attach to the connection holes of the targeting guide.

Yet another aspect of the present disclosure includes a method that includes the steps of selecting between a first bone plate and a second bone plate, the first and second bone plates having different patterns of bone plate holes; selecting between a plurality of sides of a targeting guide based on the selected bone plate; attaching the targeting guide to the selected bone plate.

DETAILED DESCRIPTION

Figure 1:
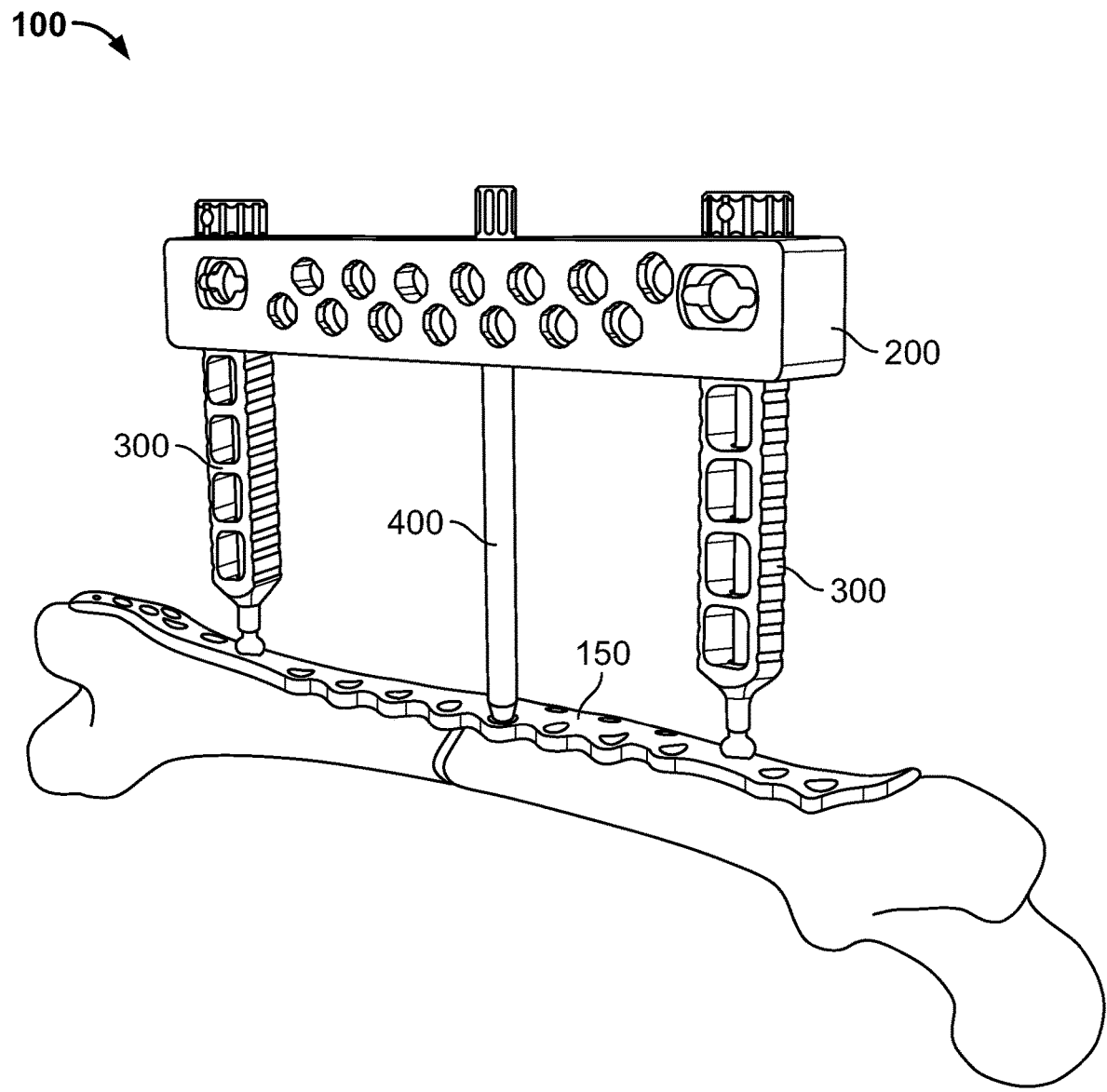
FIG. 1 is a schematic perspective side view of a targeting guide system in accordance with a first embodiment of the present disclosure shown in conjunction with a femur bone plate.

The present invention generally relates to a targeting guide system to be used in conjunction with a bone plate and screws for monoaxial screw placement of the bone plate on the bone. Those of skill in the art will recognize that the following description is merely illustrative of the principles of the invention, which may be applied in various ways to provide many different alternative embodiments.

In describing certain aspects of the inventions disclosed herein, specific terminology will be used for the sake of clarity. However, the inventions are not intended to be limited to any specific terms used herein, and it is to be understood that each specific term includes all technical equivalents, which operate in a similar manner to accomplish a similar purpose. In the drawings and in the description which follows, when referring to the term "proximal" in the context of the bone, the term "proximal" refers to the end of the bone plate or targeting block that is closer to the heart, while the term "distal" refers to the end of the bone plate or targeting block that is further from the heart. In the drawings and in the description which follows, when referring to the term "proximal" refers to the end of the instrumentation, or portion thereof, which is closest to the operator in use, while the term "distal" refers to the end of the instrumentation, or portion thereof, which is farthest from the operator in use.

The tools described below are designed to facilitate efficient and accurate screw insertion during surgery. FIGS. 1-14 depict a targeting guide system 100 including a targeting block 200, supports or handles 300, and instrumentation 400. Targeting guide system 100 is designed to facilitate the accurate placement of screws within holes of bone plates and into engagement with the bone. In some instances, the trajectory of the bone screw placement may be monoaxial, or along one single axis, and in other instances, it is contemplated, that the trajectory of the bone screw placement may be polyaxial, along more than one axis. The system is configured to correspond to any type of bone plate, and is particularly useful where at least two bone plates having different lengths from one another and/or left and right plate versions are included. The different cooperations between the guide and the plates being achieved through rotation of the targeting guide, for instance, with different bone plate sizes and/or shapes being engageable upon 90 degrees rotation of the guide, and the right-left configuration being engageable upon 180 degrees rotation.

The targeting systems disclosed herein are designed for use on any bones. Specifically, the targeting guide blocks are configured for connection to any type of plate.

In FIG. 1 the targeting system is shown as an example with a femur bone plate for use with femur fractures. Specifically, in FIG. 1, the targeting guide system of the present disclosure is shown with an interprosthetic femur plate, although the system may be used with other femur plates, including proximal femur plates and distal femur plates, as well as plates designed for other bones. In certain instances, such as for example with the use of interprosthetic and proximal femur plates, such targeting guides may be also used for plates that are peri-prosthetic.

Figure 2:
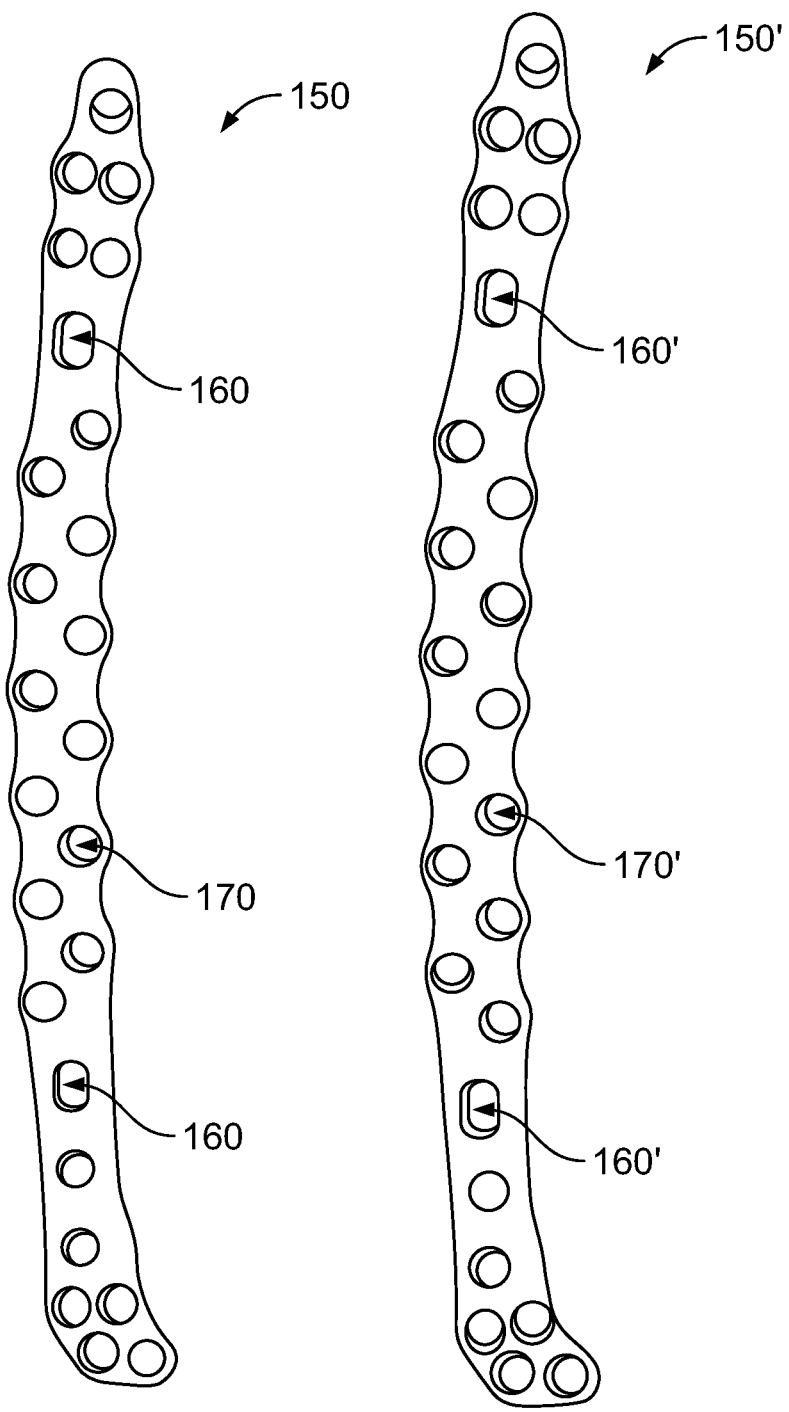
FIG. 2 is a front view of two alternative bone plates to be used with the system of FIG. 1.

FIG. 2 shows plates 150, 150' each including a plurality of screw holes 170, 170' for polyaxial or monoaxial placement of screws within the holes. Each hole 170 includes a central axis extending in the direction from the upper and lower surfaces of the plate. Plates with such holes are described in further detail in U.S. Patent Publication No. 2019/0269445, entitled Bone Plates and Associated Screws, filed on Mar. 1, 2019. Plate 150 and plate 150' are substantially similar except that plate 150' has a greater length than plate 150'. As a result, plate 150 and plate 150' have a different arrangement of holes 170, 170' due to the difference in length. Namely, plate 150 has twelve holes 170 positioned between oblong holes 160 and arranged in six pairs of diagonal holes; whereas, plate 150' has thirteen holes 170' positioned between oblong holes 160' with six pairs of diagonal holes and an additional hole. As described herein, targeting guide system 100 facilitates accurate insertion of the screws within holes 170, 170' of plates 150, 150'. Further, plates 150, 150' each include at least one oblong hole 160, 160' for connection of a support or handle, as will be discussed in further detail below. Plates 150, 150' are both interprosthetic plates designed to be connected to the bone between total hip and total knee arthroplasties, and each plate 150, 150' includes two oblong holes; whereas, for proximal and distal plates, the plates generally include one oblong hole, shown in FIG. 15, and discussed in further detail below. In the examples shown, the oblong holes of the plate, form a connection point between the plate and the block via a handle. Thus, as described in further detail below, plates with one oblong hole are described with one handle, and plates with two oblong holes are described with two handles each being connected at a respective one of the two oblong holes.

Figure 3:
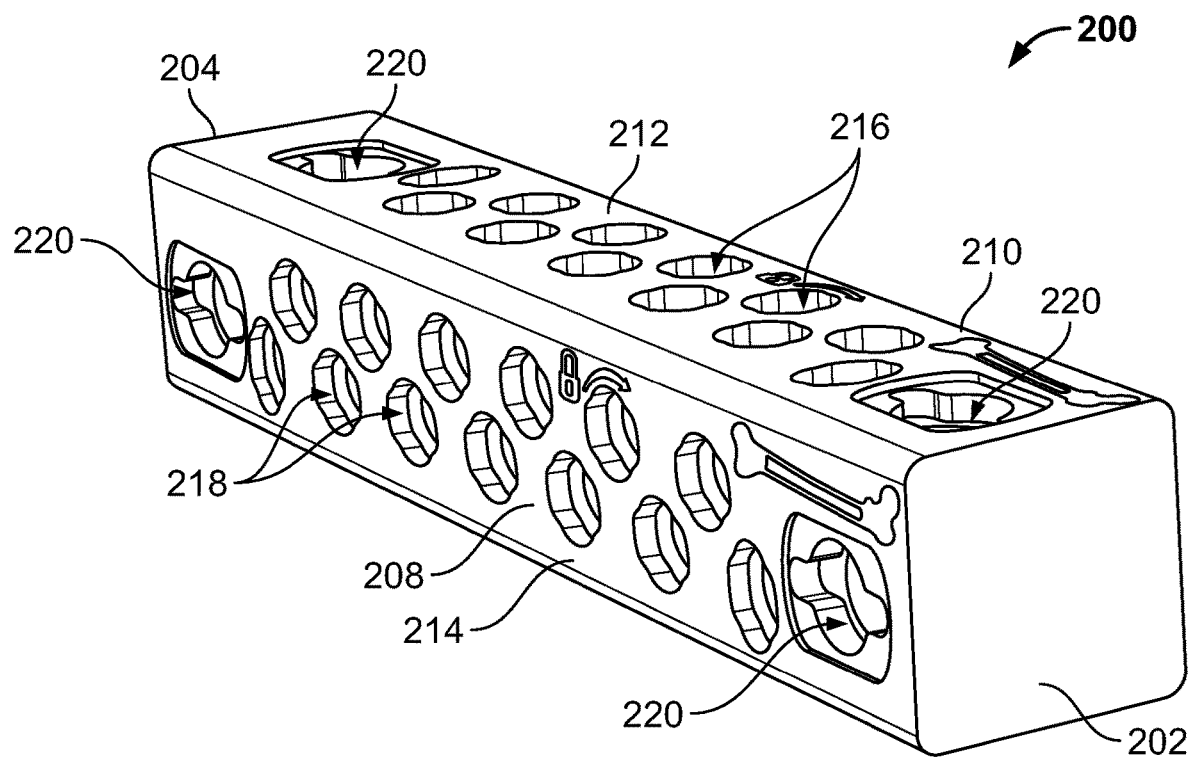
FIG. 3 is a perspective side view of the targeting block of the guide system of FIG. 1.
Figure 4A:
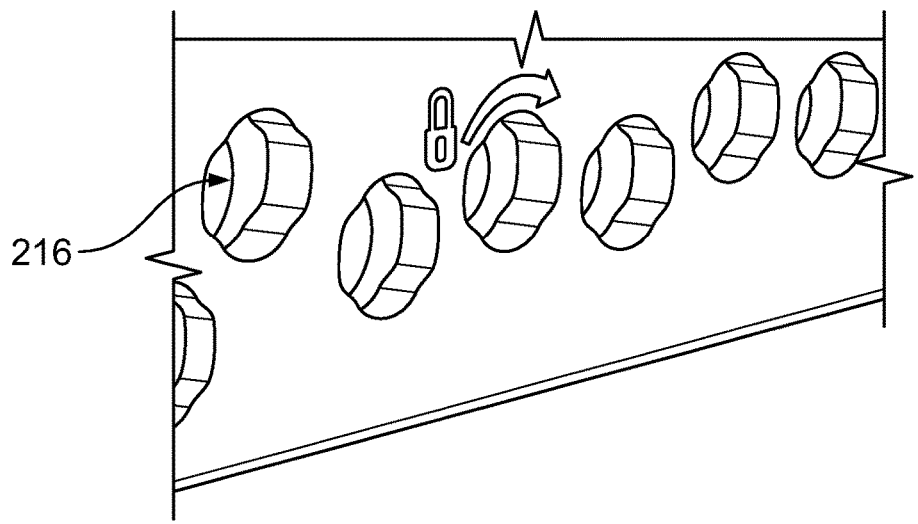
FIG. 4A is an enlarged view of the screw holes of the targeting block of FIG. 3
Figure 4B:
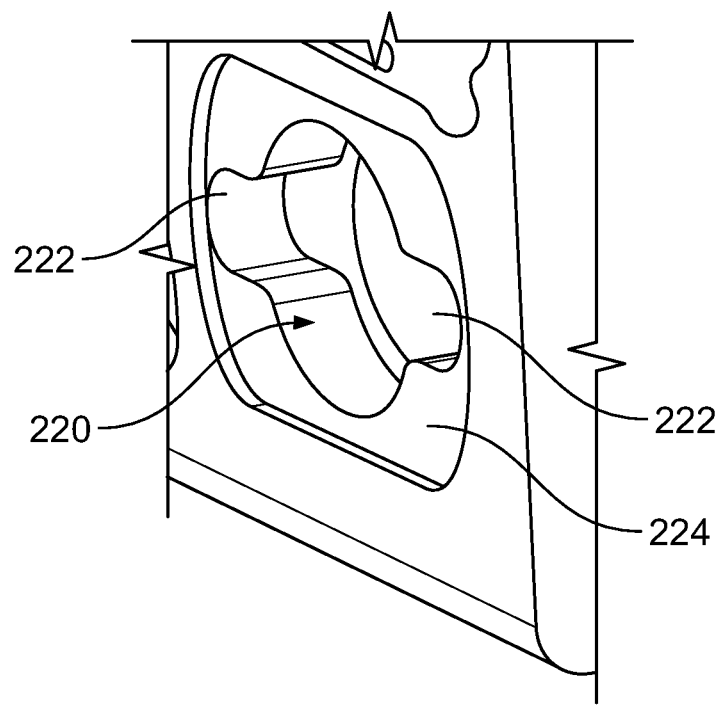
FIG. 4B is an enlarged view of the connection holes of the targeting block of FIG. 3.

Turning to FIGS. 3, 4A and 4B, targeting guide is in the form of block 200 shown as having the shape of a rectangular prism with six rectangular faces. With reference to FIG. 3, targeting block 200 extends between a proximal end 202 and distal end 204, corresponding to the relative positioning of the bone plate on the bone. A length of block 200 is defined between proximal and distal ends 202, 204. Block 200 includes upper side 212 and opposing lower side 214, and block 200 further includes first lateral side 208 and an opposing lateral side 210, each extending between upper side 212 and lower side 214.

Each of the upper and lower sides 212, 214 and first and second lateral sides 208, 210 define a first connection hole 220 extending therethrough at proximal end 202 and a second connection hole 220 at distal end 204. FIG. 4B shows connection hole 220, which is configured for connection to a handle to allow the block 200 to connect to both plates 150, 150'. Each connection hole 220 is positioned within a cavity portion 224 which is recessed from the adjacent surface of the block. Further, each connection hole 220 is substantially round with two elongate wings 222 extending in the proximal-distal direction of the block, shown in FIG. 4B.

As shown in FIG. 3, block 200 includes a plurality of first holes 216 extending through the upper and lower sides and along a portion of the length of block 200 between first and second connection holes 220A. Each first hole 216 has a central axis extending in the direction of the upper and lower sides of the block. Block 200 further includes a plurality of second holes 218 extending through the first and second lateral sides and along a portion of the length of the block 200 between first and second connection holes 220B. Each second hole 218 has a central axis extending in the direction of the first and second lateral sides of the block.

First holes 216 and second holes 218 are identical in shape, and have a substantially circular shape. In particular, as shown, the holes are mostly circular and may have at least two opposing flat sides (best shown in FIG. 4A).

The plurality of first holes 216 are arranged in a first pattern that is different from a second pattern in which the plurality of second holes 218 are arranged. Namely, the first pattern corresponds to and matches the holes 170 of a first bone plate 150 having a first length, and the second pattern corresponds to and matches the holes 170' of a second bone plate 150' having a second length different from the first length. For example, as shown in FIG. 3, holes 216 are arranged in a pattern including six diagonal pairs of holes 216 so as to correspond to the holes 170 of the shorter plate 150; whereas, holes 218 are arranged in a pattern including six diagonal pairs of holes 218 and a thirteenth hole so to correspond to holes 170' of the longer plate 150'.

Thus, block 200 can be attached to the bone with upper and lower sides 212, 214 extending parallel to the bone to attach to and fix bone plate 150 to bone. Block 200 can be rotated 90 degrees such that first and second lateral sides 208, 210 extend parallel to the bone. In this configuration, block 200 is attached to and facilitates the fixing of bone plate 150' to the bone. In this manner, each block 200 accommodates two different bone plates. In this example, the bone plates have different lengths and different patterns of screw holes thereon; however, it is contemplated that that the bone plates may have different shapes, profiles and screw hole designs from one another as well.

Moreover, block 200 is designed for use with both the left and right sides of the body. For example, block 200, as shown in FIG. 3, with first lateral side 208 positioned upward such that the first lateral side extends parallel to the bone, and second lateral side 210 is relatively closer to the bone than is first lateral side 208, the block 200 is configured to attach a bone plate 150' to the left femur of a patient. This is identified on the first lateral side 208, which is marked with "LEFT" to allow surgeons with easy identification. Rotation of block 200 180 degrees, such that second lateral side 210 is upward and first lateral side 208 is relatively closer to the bone than is second lateral side 210, allows for connection of block 200 to bone plate 150' to the right femur of a patient.

Rotation of block 200 by 90 degrees allows for use of a different plate, which in the example shown, has a different length. Additionally or alternatively, the blocks may cooperate with two different bone plates that each have a different peripheral shape and/or different screw hole designs and screw hole sizes. Rotation of block 200 by 180 degrees allows for use of the block with both the right and the left side of the body. Thus, a single block 200 is usable with four different plates, the left and right of a first plate of a first size, and the left and right of a second plate of a second size.

As noted above, block 200 includes indicia, such as indication as to the correct orientation of the guide for left and right versions of a given plate size. Moreover, block 200, as shown, includes an indication of the orientation of the guide with respect to the "Proximal Side" and "Distal Side" of the plate, as well as an indication of the type of plate ("Interprosthetic" in the version shown) along with plate size on different sides of the block indicating orientation with respect to a given plate size.

Figure 5:
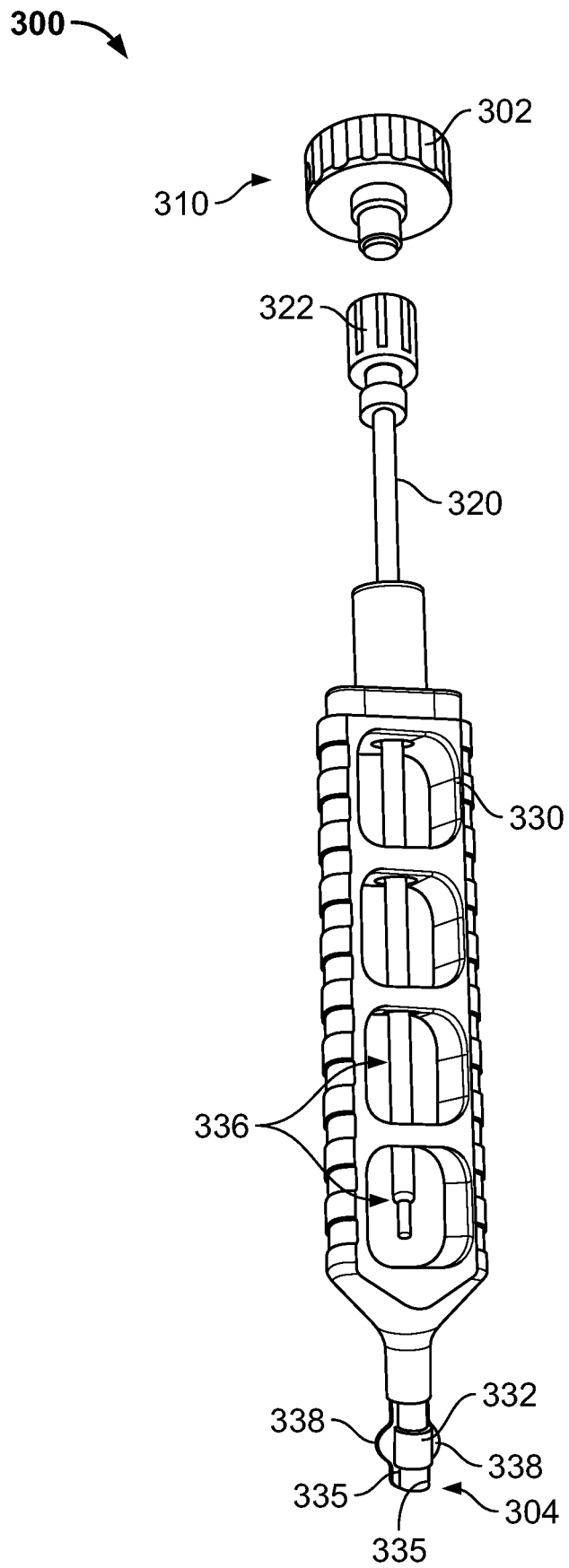
FIGS. 5 and 6 are side views of a support or handle of the guide system of FIG. 1.
Figure 6:
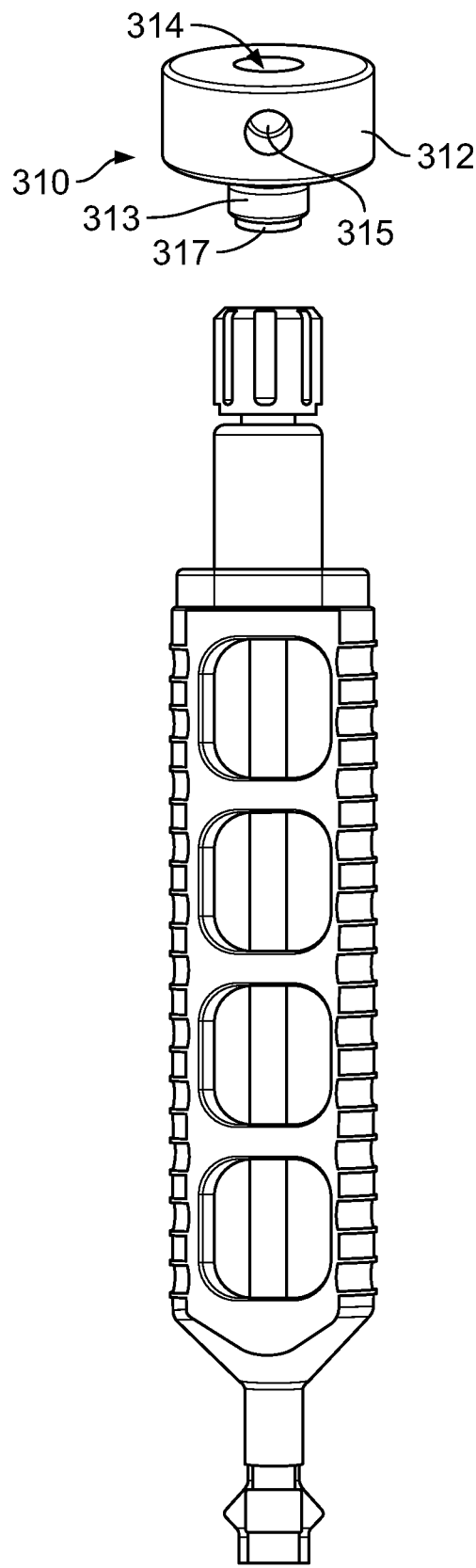

Turning to FIG. 5, handle 300 is shown which facilitates the connection of block 200 to a bone plate 150. Handle 300 includes wheel 310, shaft 320 and grip 330. Handle 330 extends between proximal end 302, closest to the operator in use, which connects to block 200, and distal end 304 which connects to oblong hole 160 of bone plate 150.

Grip 330 defines the portion of the handle for the surgeon to hold and manipulate and defines a cannulation through the length of the grip for receiving shaft 320. Grip 330 defines at least one window 336 for viewing the shaft 320. In the illustrated example, grip 330 includes four windows 336. Distal end 304 includes engagement portion 332 which is designed to be received within oblong holes 160 of bone plate 150. Engagement portion 332 has a necked portion defined by wings 338 such that the diameter of the engagement portion is greater across wings 338 than at the adjacent distal end. Further, engagement portion 332 includes flexure strips 335 extending in the proximal-distal direction of handle 300 to allow the engagement portion 332 to flex into the oblong hole 160.

Shaft 320 is positioned within the cannulation of grip 310 in order to securely fix the handle 300 to the bone plate 150. Shaft 320 includes knob 322 at a proximal end of the shaft, the knob 322 can be rotated in order to thread the shaft to handle 300, which spreads distal end 304 of handle 300. The expansion of distal end 304 fixes the handle within oblong hole 160 of plate 150. With the shaft 320 and grip 330 secured to one another via the threading, knob 322 abuts the proximal end of the grip 330. Knob 322 is configured to engage connection holes 220 of block 200.

Handle 300 further includes wheel 310 defines cannulation 314 therethrough and further includes cap 312 at a proximal end of the wheel and connection element 313 extending distally from the cap 312. Connection element 313 is configured to be received within connection holes 220 of block 200 and within knob 322 of shaft 320 to fix the wheel to the shaft-grip assembly. Connection element 313 includes thread 317 for threading engagement with a proximal end of the knob 322 of shaft 320. Wheel 310 further includes through hole 315 extending through cap 312 in a direction oblique to cannulation 314. Through hole 315 is configured to receive a driver, which can increase the arm in order to rotate wheel 310 during connection to block 200 and the shaft-grip assembly.

Figure 7:
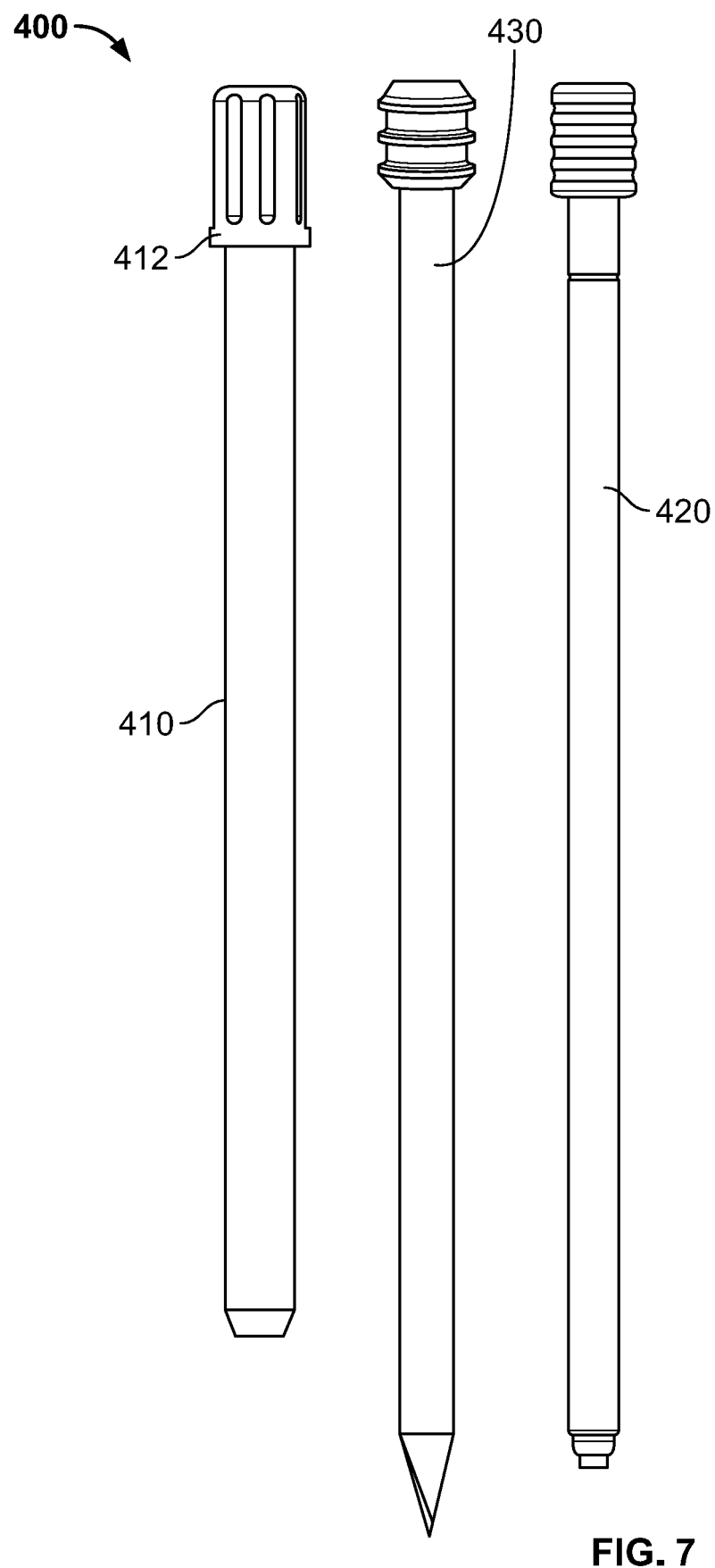
FIG. 7 are front views of instrumentation used in conjunction with the system of FIG. 1.
Figure 8:
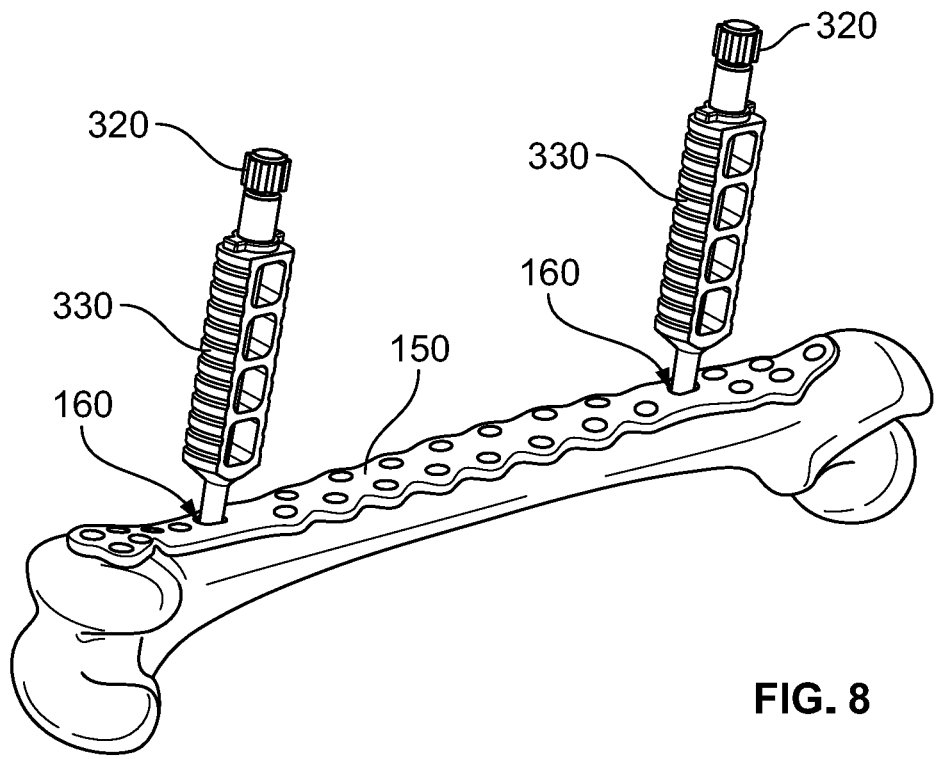
FIG. 8 is a schematic perspective side view of the handles and bone plate of the system of FIG. 1 with a femur bone.

Targeting system 100 also includes various instrumentation, including guiding sleeves, for allowing for accurate and safe placement of the screws within holes 170 of bone plate 150 and into bone. Such instrumentation are shown in FIG. 7, although will be described in greater detail below with regard to their function during the use of targeting guide system 100. As shown in FIG. 7, system 100 includes a set of instruments 400 that includes among other tools, described in detail below, tissue protection sleeve 410, drill sleeve 420 and trocar 430. Tissue protection sleeve 410 alone or in combination with drill sleeve 420 facilitate monoaxial placement of screws within the sleeve, through the guide block, and into holes 170 of the bone plate at a single axis. Tissue protection sleeve 410 includes an outer flange 412 at a proximal end thereof to be received within holes 216, 218 of block 200 and enable tissue protection sleeve to be locked within the holes to prevent movement. In other examples, tissue protection sleeve 410 and holes 216, 218 are sized to allow movement of the tissue protection sleeve within the hole at a plurality of axes, angled relative to the central axis of the holes 216, 218 to accommodate placement of the screws at a plurality of axes relative to holes 216, 218 and bone plate holes 170.

FIGS. 8-13 show targeting guide system 100 in use on a femur bone. With bone plate 150 positioned against bone, handles 300 are each attached to oblong holes 160 of the bone plate 150 at engagement portion 332 of grip 330. Shaft 320 is positioned within grip 330 and tightened to establish a solid link between the plate and the shaft-grip assembly, shown in FIG. 8. This step is performed twice to attach the two handles to the two oblong holes 160 of the plate 150.

The user chooses the appropriate block 200 as well as the appropriate sides of the block, i.e. upper and lower sides or lateral sides, which will be used as the aiming guide for the bone plate holes. Based on the size of the bone plate, the block 200 can be rotated 90 degrees and based on whether the plate is the left side or the right of the body, the block 200 can be rotated 180 degrees.

Figure 9:
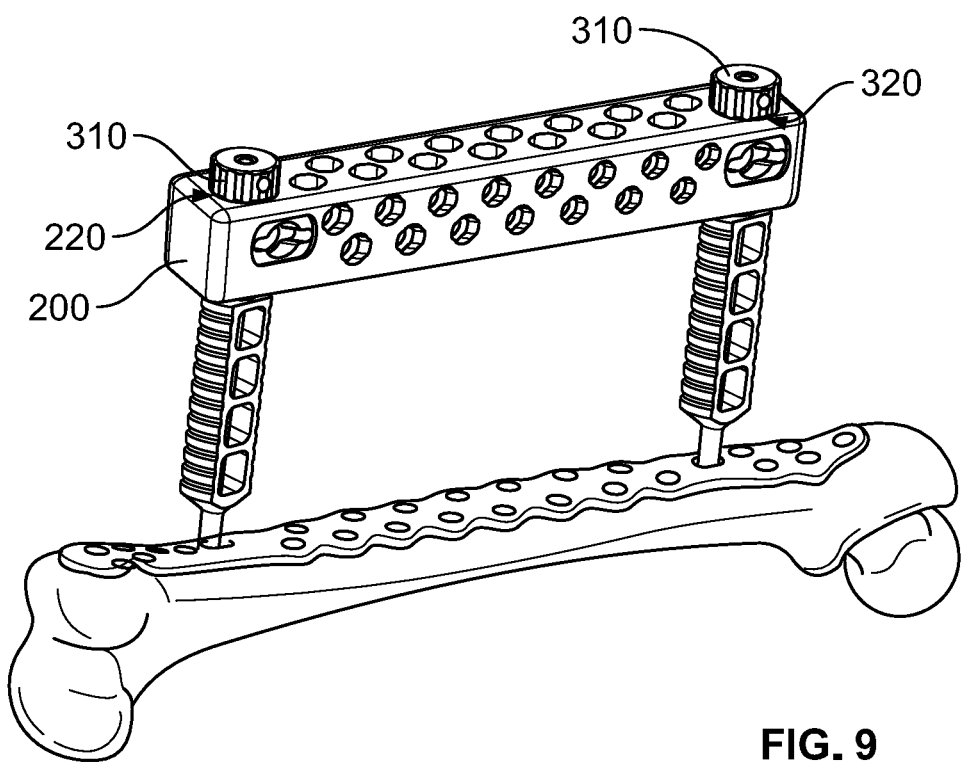
FIG. 9 is a schematic perspective side view of the handles, block, and bone plate of the system of FIG. 1 with a femur bone.
Figure 10:
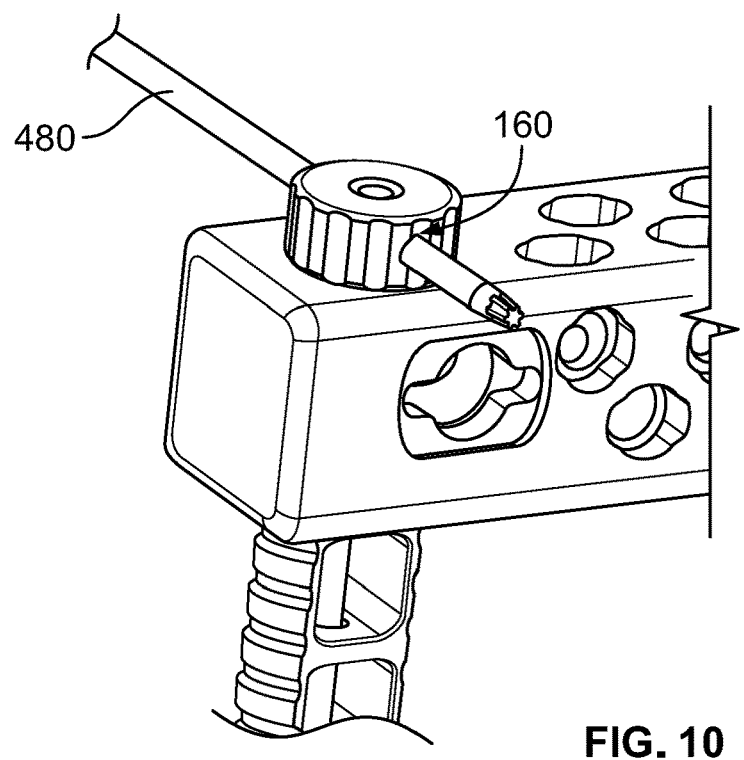
FIG. 10 is an enlarged view of the wheel of the handle of FIG. 6 in conjunction with the block of FIG. 3.

With the necessary side extending parallel to the bone, the user inserts cap 322 of shaft 320 within one of the connection holes 220 at the bottom side, i.e. the side parallel to and closest to the bone. FIG. 9 shows each wheel 310 placed within one of the two connection holes 220 on the top side, i.e. the side parallel to and furthest away from the bone, and rotated to connect the wheel 310 to the block 200 and to shaft 320. As shown in FIG. 10, a driver 480 can be placed within through hole 315 to create a longer arm for easier rotation of the wheel. Both supports or handles 300 are connected and the targeting block 200 is positioned above and aligned with the bone plate 150 such that respective holes 216 (or 218 depending on the position of the block) align with the respective hole 170 of plate 150. In this manner, the central axis of a hole 216 is coaxial with the corresponding central axis of the respective hole 170 of plate 150.

Figure 11:
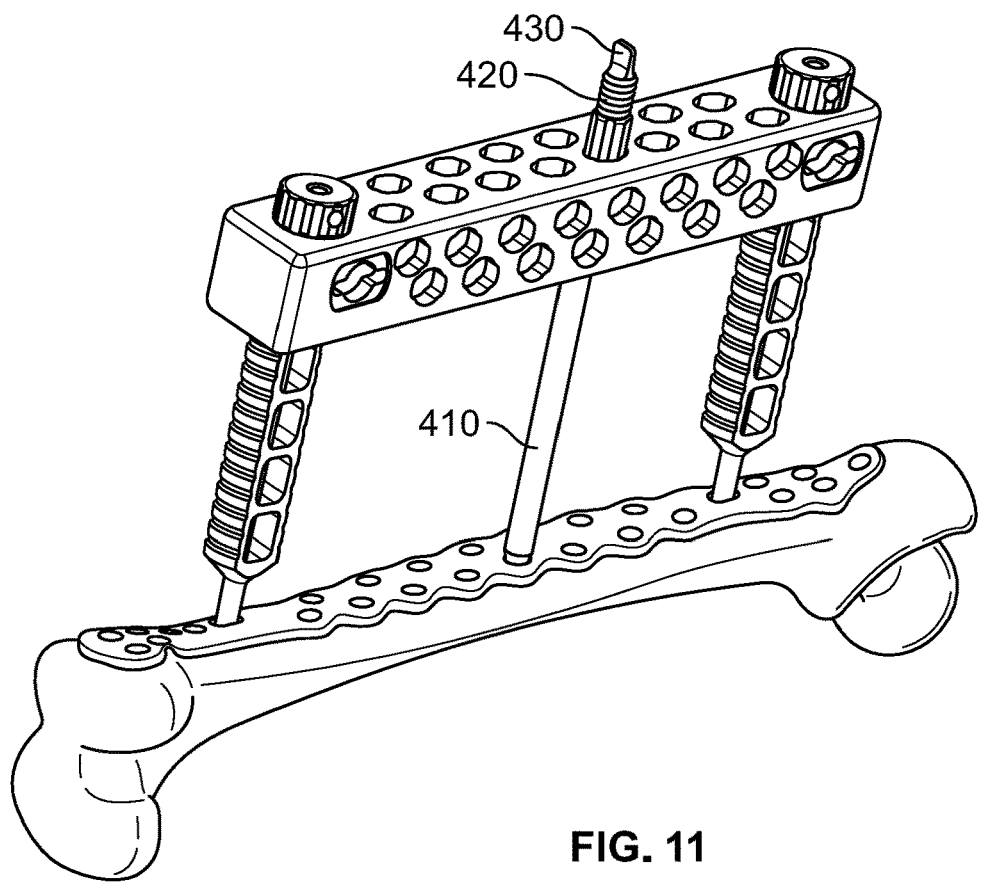
FIGS. 11 and 12 are schematic perspective side views of the handles, block, instrumentation, and bone plate of the system of FIG. 1 with a femur bone.

Trocar 430 is inserted into drill sleeve 420 and the assembly is inserted into tissue protection sleeve 410, which is a monoaxial sleeve. As shown in FIG. 11, tissue protection sleeve 410 is then placed within a hole 216 (or 218 depending upon which side of the block is utilized, but for simplicity only hole 216 will be used for the description of use) and the corresponding hole 170 of plate 150. Tissue protection sleeve 410 is rotated to lock the tissue protection sleeve into hole 216 and then guided into hole 170 of the bone plate.

Figure 12:
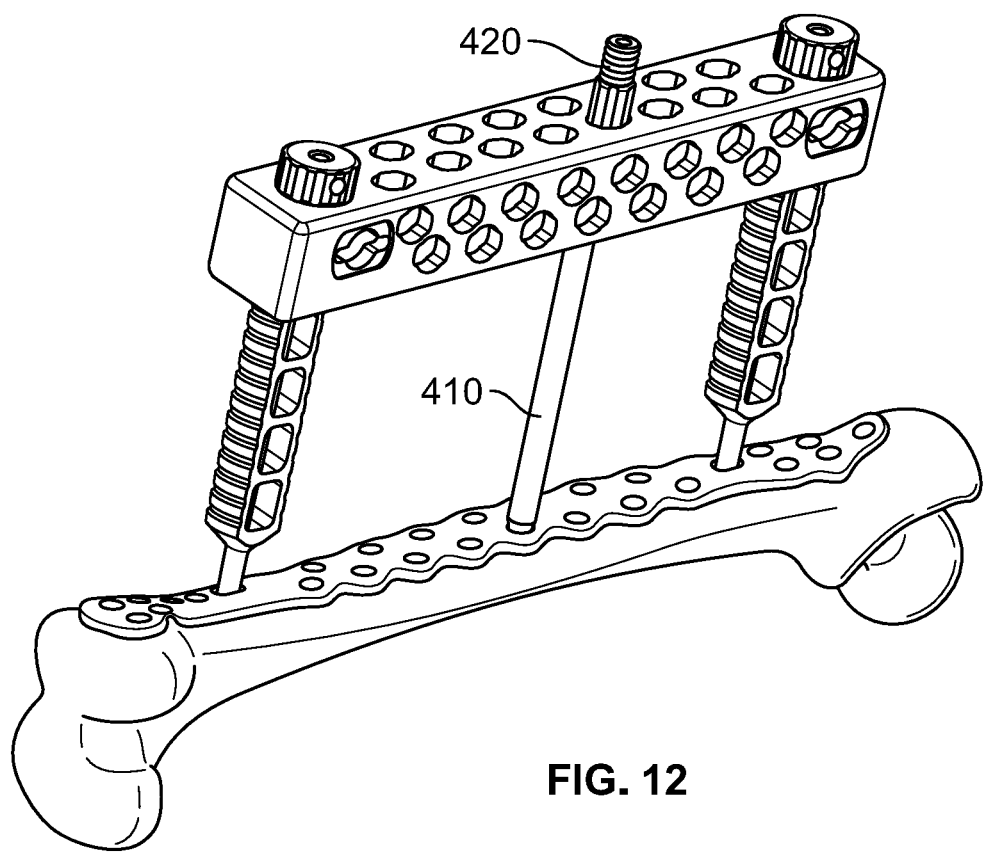
Figure 13:
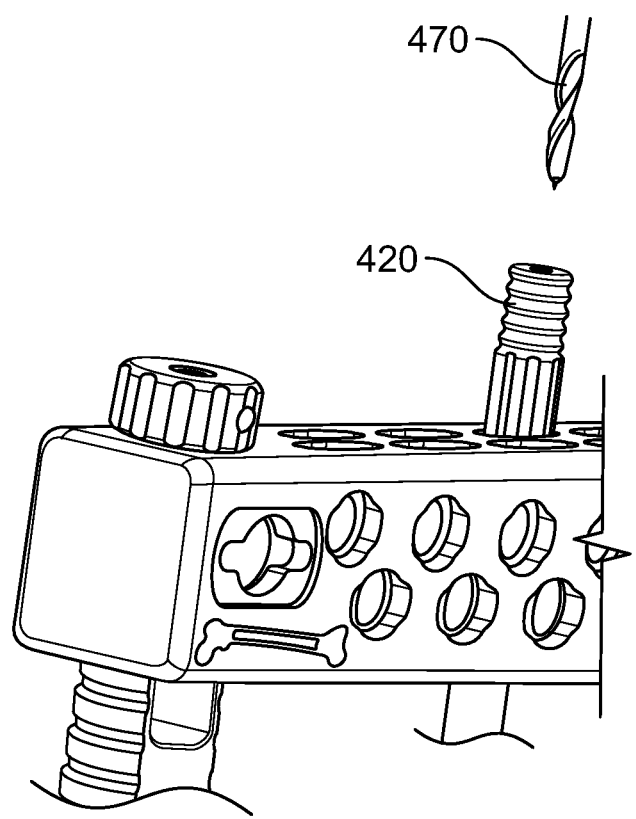
FIG. 13 is an enlarged view of the drill sleeve, tissue protection sleeve and drill of the targeting guide system of FIG. 1.

Trocar 430 is then removed in order to begin drilling of the screw hole into bone. FIGS. 12 and 13 show drill sleeve 420 and tissue protection sleeve 410 within hole 216 of block 200. Drill bit 470 is positioned within drill sleeve 420 and torqued to form the hole into which a locking or non-locking screw will be implanted.

Figure 14:
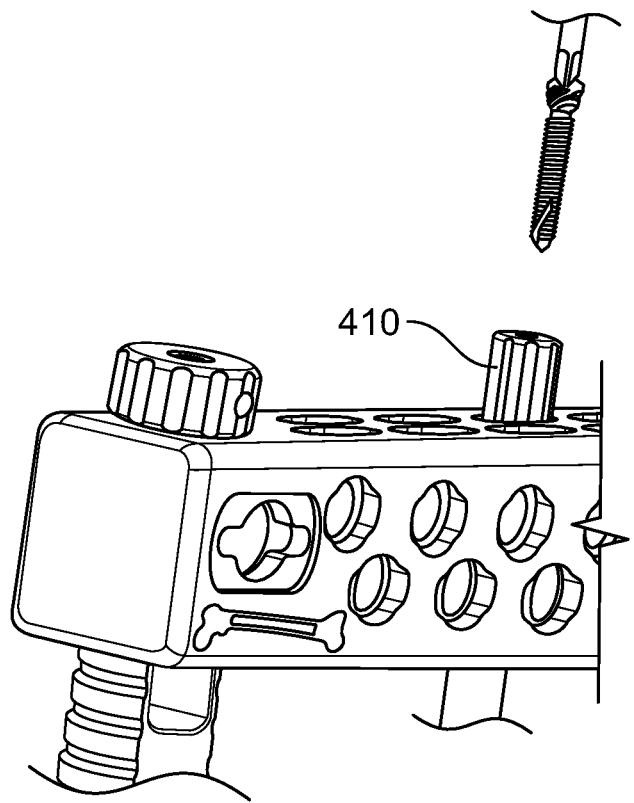
FIG. 14 is an enlarged view of a screw in conjunction with the tissue protection sleeve and block of the targeting guide system of FIG. 1.

Drill sleeve 420 is removed prior to tapping or screw insertion. A screwdriver, with screw attached, shown in FIG. 14, is placed within tissue protection sleeve and to fix the screw in the bone along the axis defined by holes 216 of block 200. In this manner, the screw is positioned along the monoaxial trajectory of the hole 216.

The sleeve assembly can be moved to various holes 216 to implant a plurality of screws through block 200 and into engagement with bone plate 150 and the bone to provide fixation of the bone plate to the bone. Each holes 216 of block 200 allows for accurate monoaxial screw placement of the locking or non-locking screws within bone plate 150.

Figure 15:
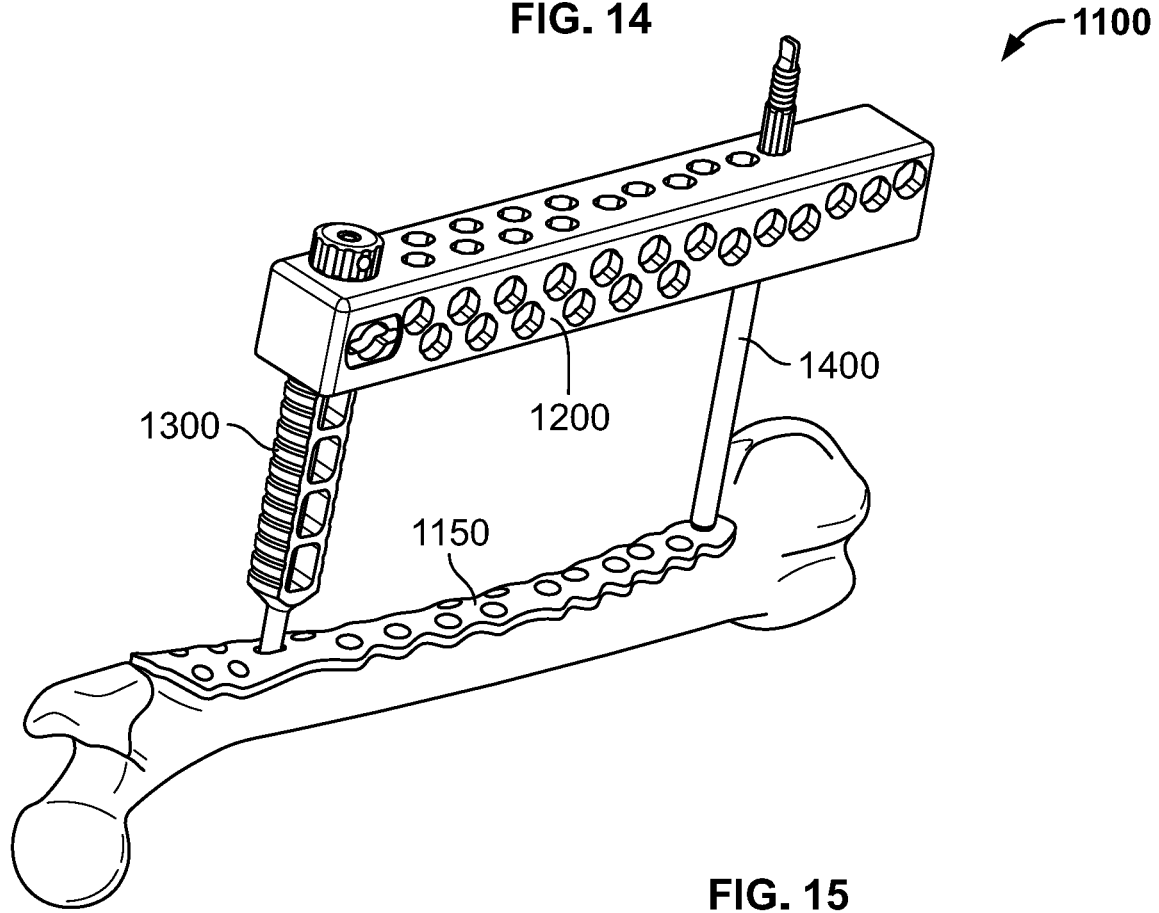
FIG. 15 is a schematic perspective side view of a targeting guide system in conjunction with a femur bone plate in accordance with another embodiment of the present disclosure.
Figure 16:
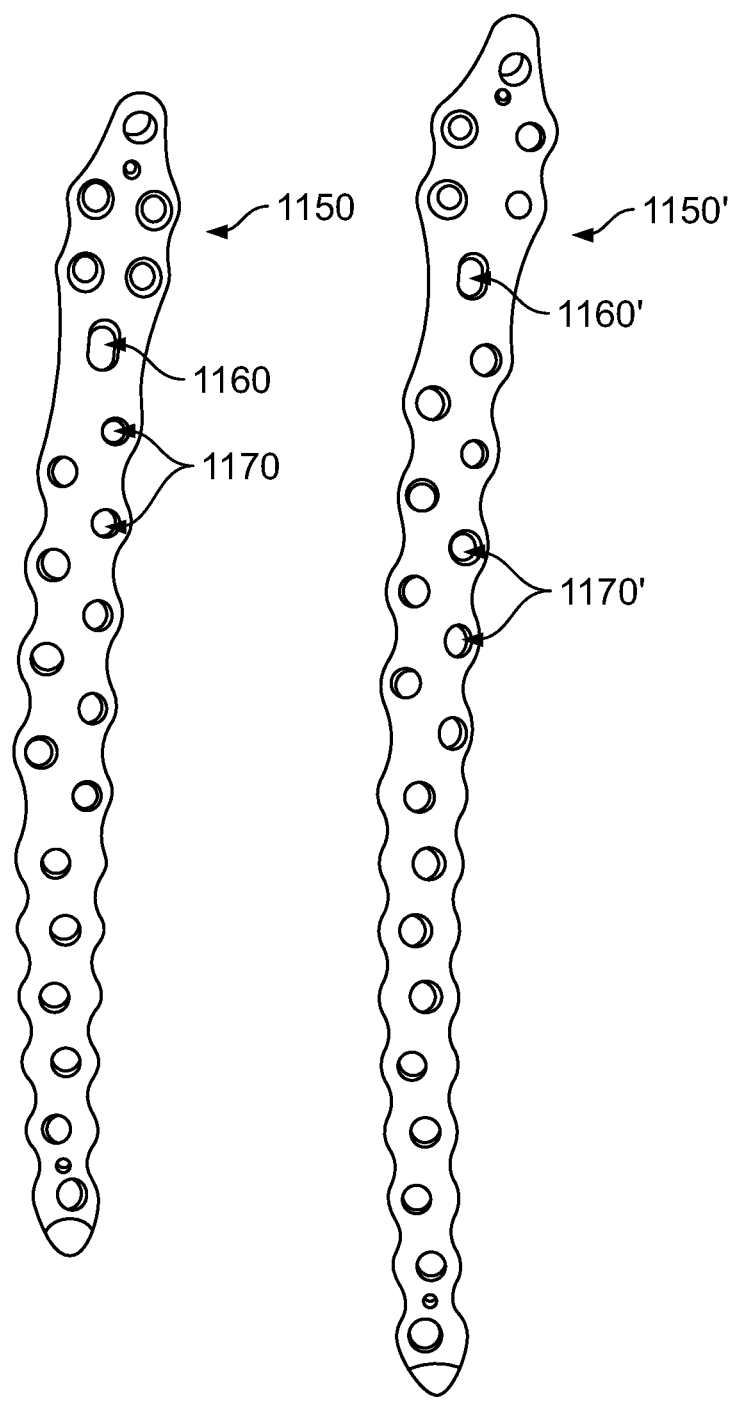
FIG. 16 is a front view of two alternative bone plates to be used with the system of FIG. 15.
Figure 17:
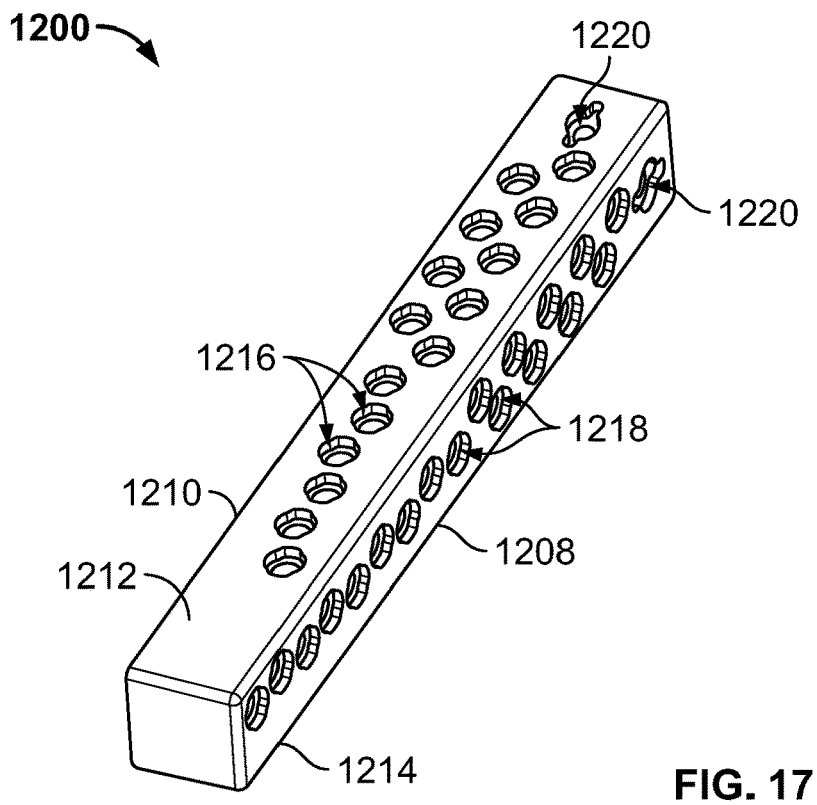
FIG. 17 is a perspective side view of the targeting block of FIG. 15.

FIGS. 15-17 show targeting guide system 1100 including targeting block 1200, bone plate 1150, handle 1300 and instrumentation 1400. Like reference numerals refer to like elements in this embodiment, but with numbers in the 1000 series, and the differences will between systems 100 and 1100 will be discussed.

System 1100 is identical to system 100 in many respects, except that system 1100 is designed to be used in conjunction with proximal and distal plates having one oblong hole 1160, as shown in FIG. 16. Therefore, the system includes one handle 1300 for connection to the one oblong hole 1160 of the plate 1150.

FIG. 16 shows plates 1150 and 1150', which are similar to plates 150, 150'. Plate 1150 has a shorter length than plate 1150', which causes the arrangement or pattern of holes 1170 to be different from the pattern of holes 1170' on plate 1150', with plate 1150' having an additional hole 1170'.

In other examples described above, the plates may also have a different outer peripheral shape or the holes of each plate may differ in other characteristics additionally or alternatively.

FIG. 17 shows targeting block 1200 which is identical to block 1200 in most respects, except that each of the upper side 1212, lower side 1214, first lateral side 1208 and second lateral side 1210 includes one connection hole 1220 rather than two as in block 200. The one connection hole 1220 is to correspond to the oblong hole 1160 of plate 1150. Like block 200, the upper and lower sides have a different arrangement of holes 1216 than the first and second lateral sides have an arrangement of holes 1218. Holes 1216 of upper and lower sides 1212, 1214 match holes 1170 of plate 1150; whereas, holes 1218 of first and second lateral sides 1208, 1210 to correspond to or match holes 1170' of the longer plate 1150'.

Referring to FIG. 15, in use, one handle 1300 connects at a distal end to the oblong hole 1160 of bone plate 1150 (as noted above, for simplicity, only bone plate 1150 will be described in the use of the system 1100) and at a proximal end to block 1200. Generally, the oblong hole is positioned on a proximal portion of the bone plate, and the connection hole of the block is positioned on a proximal end of the block. At the distal end of the block, sleeve assembly 1400 is attached to block 1200 and plate 1150, as described above with reference to FIG. 11. Sleeve assembly 1400 is identical to sleeve assembly 400 described with reference to system 100 and includes a trocar, drill sleeve and tissue protection sleeve. Sleeve assembly 1400 may be attached to the most distal hole 1216 of block 1200, as shown in FIG. 15, or it may be attached to a different hole on the distal portion of the block 1200.

Figure 18:
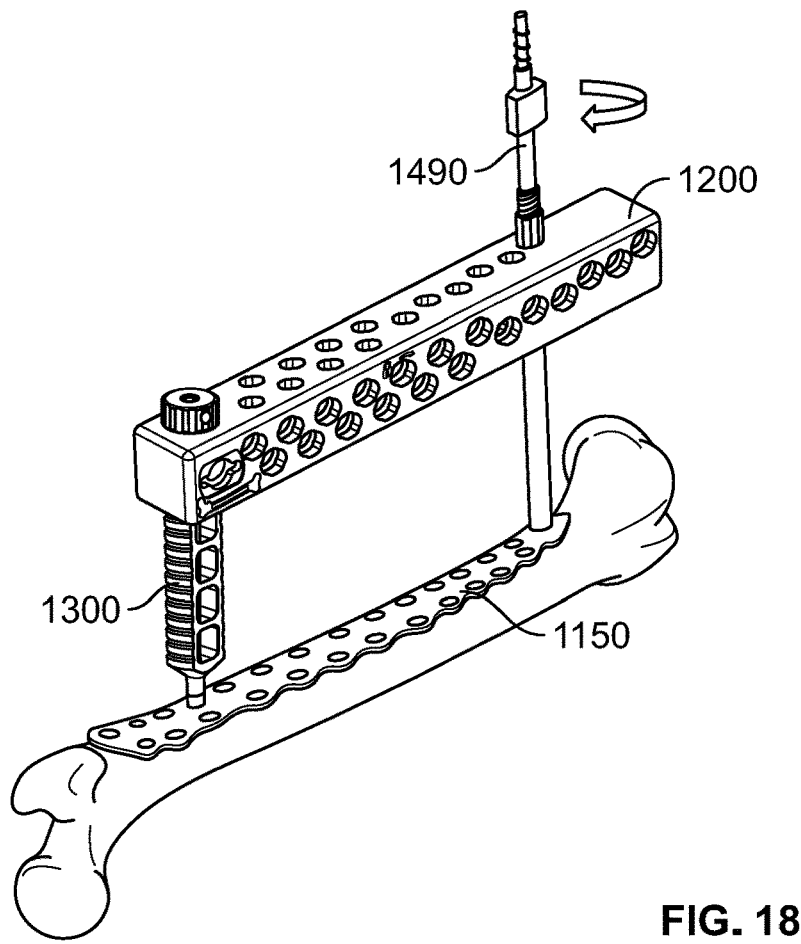
FIG. 18 is a schematic perspective side view of the targeting guide system of FIG. 1 with a temporary plate fixator.
Figure 19:
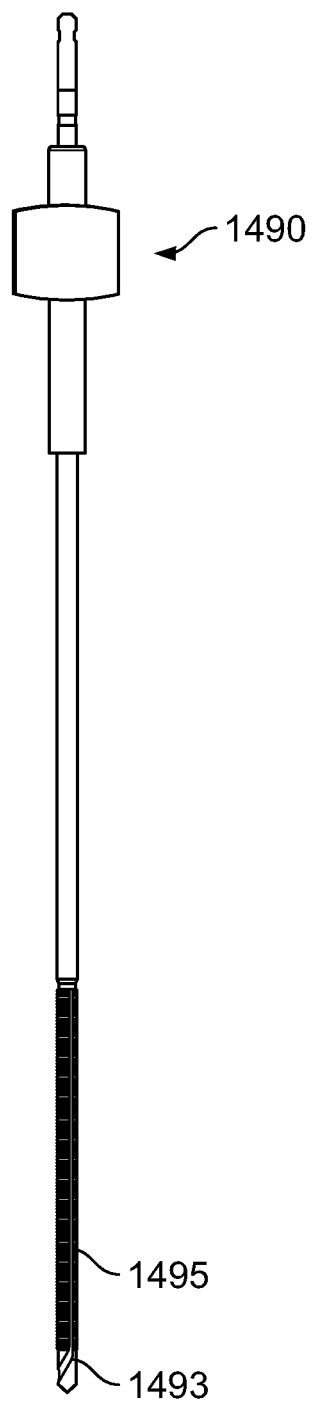
FIG. 19 is a front view of the temporary plate fixator of FIG. 18.

The trocar is then removed and temporary plate fixator 1490 is positioned through the drill-tissue protection sleeve assembly, as shown in FIG. 18. The temporary plate fixator 1490 has a threaded shaft 1495 and a self-drilling, self-tapping tip 1493 for quick insertion into cortical bone, shown in FIG. 19. Temporary plate fixator 1490 is rotated in a clockwise direction (as shown by the arrow) to tension block 1200 to plate 1150. This creates a stable attachment of block 1200 to plate 1150. With the distal end of block 1200 attached to plate 1150, an additional tissue protection sleeve and drill sleeve may be needed, in the similar manner as described above in connection to placing the other screws within plate 150.

As described above with reference to FIGS. 11-14, screws can be inserted into the additional holes 1216 of block 1200 and holes 1170 of plate 1150 to fix the plate to bone with accurate placement of the screws.

The targeting guide blocks of the present disclosure are formed from milled carbon fiber reinforced polyetherimide. Examples of dimensions of the blocks disclosed herein include a height and width both of about 42 mm and a length of about 181 mm to about 334 mm. However, such lengths of the desired block may be chosen based on the length of the desire plate. In certain examples, the blocks may be designed using three-dimensional printing. In some cases, the blocks may be made for single use.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of aligning a targeting guide with a bone plate comprising:

physically aligning a first targeting guide pattern of holes extending through upper and lower sides of a body of the targeting guide with a first plate pattern of holes of a first bone plate, the targeting guide including the first targeting guide pattern of holes and a second targeting guide pattern of holes extending through first and second lateral sides of the body, the first and second lateral sides connecting the upper and lower sides and being substantially perpendicular to the upper and lower sides such that an axis of each hole of the second targeting guide pattern of holes extends from the first lateral side through the second lateral side, wherein the axis of each hole of the second targeting guide pattern of holes is coaxial with an axis of a corresponding one of a second plate pattern of holes of a second bone plate when the targeting guide is attached to the second bone plate.

2. The method according to claim 1, further comprising inserting a drill bit through the first targeting guide pattern of holes and the first plate pattern of holes.

3. The method according to claim 2, further comprising inserting bone screws through the first targeting guide pattern of holes and the first plate pattern of holes.

4. A method of aligning a targeting guide with a bone plate comprising:

physically aligning a first targeting guide pattern of holes extending through upper and lower sides of a body of the targeting guide with a first pattern of plate holes of a first bone plate, the targeting guide including the first targeting guide pattern of holes and a second targeting guide pattern of holes arranged in a different second pattern and extending through first and second lateral sides of the body, the first and second lateral sides connecting the upper and lower sides and being substantially perpendicular to the upper and lower sides such that an axis of each hole of the second targeting guide pattern of holes extends from the first lateral side through the second lateral side, wherein the axis of each hole of the second targeting guide pattern of holes is coaxial with an axis of a corresponding one of a second pattern of plate holes of a second bone plate when the targeting guide is attached to the second bone plate.

5. The method according to claim 4, wherein the physically aligning step includes aligning the first targeting guide pattern of holes coaxial with the first pattern of plate holes of the first bone plate.

6. The method according to claim 4, wherein the physically aligning step includes aligning the second targeting guide pattern of holes coaxial with the second pattern of plate holes of the second bone plate.

7. The method according to claim 4, further comprising inserting a sleeve through a hole of the first targeting guide pattern of holes and a hole of the first pattern of plate holes of the first bone plate.

8. The method according to claim 4, further comprising inserting a sleeve through a hole of the second targeting guide pattern of holes and a hole of the second pattern of plate holes of the second bone plate.

9. The method according to claim 4, further comprising rotating the body of the targeting guide about its longitudinal axis.

* * * * *